United States Patent [19]

Mulvaney, III et al.

[11] Patent Number: 5,744,680

[45] Date of Patent: Apr. 28, 1998

[54] PROCESS FOR PRODUCING LIGHT OLEFINS

[75] Inventors: Robert C. Mulvaney, III, Arlington Heights; Terry L. Marker, Warrenville, both of Ill.

[73] Assignee: UOP, Des Plaines, Ill.

[21] Appl. No.: 513,649

[22] Filed: Aug. 10, 1995

[51] Int. Cl.[6] ........................................... C07C 1/20
[52] U.S. Cl. ........................ 585/640; 585/638; 585/639
[58] Field of Search ............................ 585/638, 639, 585/640

[56] References Cited

U.S. PATENT DOCUMENTS

| | | | |
|---|---|---|---|
| 3,928,483 | 12/1975 | Chang et al. | 260/668 R |
| 4,025,575 | 5/1977 | Chang et al. | 260/682 |
| 4,052,479 | 10/1977 | Chang et al. | |
| 4,440,871 | 4/1984 | Lok et al. | 502/214 |
| 4,447,669 | 5/1984 | Hamon et al. | 585/640 |
| 4,496,786 | 1/1985 | Santilli et al. | 585/640 |
| 4,499,314 | 2/1985 | Seddon et al. | 585/408 |
| 4,543,435 | 9/1985 | Gould et al. | 585/330 |
| 4,547,616 | 10/1985 | Avidan et al. | 585/640 |
| 4,677,242 | 6/1987 | Kaiser | 585/638 |
| 4,677,243 | 6/1987 | Kaiser | 585/638 |
| 4,814,541 | 3/1989 | Lewis | 585/640 |
| 4,843,183 | 6/1989 | Inui | 585/640 |
| 4,861,938 | 8/1989 | Lewis et al. | 585/640 |
| 4,973,792 | 11/1990 | Lewis et al. | 585/638 |
| 5,095,163 | 3/1992 | Barger | 585/640 |
| 5,126,308 | 6/1992 | Barger et al. | 502/214 |
| 5,191,141 | 3/1993 | Barger et al. | 585/640 |

FOREIGN PATENT DOCUMENTS

WO 9313013  7/1993  WIPO.

*Primary Examiner*—Elizabeth D. Wood
*Attorney, Agent, or Firm*—Thomas K. McBride; John G. Tolomei; Richard P. Silverman

[57] ABSTRACT

A process is provided for the production of light olefins from an oxygenate feedstream. The oxygenate feedstream in the presence of a diluent is passed to a reaction zone containing a SAPO catalyst selective for the conversion of at least a portion of the feedstock into light olefins producing a reactor effluent comprising water, methane, and light olefins. The water is removed and the remaining reactor effluent is separated into a light fraction comprising methane and a light olefin stream. At least a portion of the light fraction is returned to be admixed with the feedstream as the diluent. This operation solves the problem of reducing water in the reaction zone which was found to adversely affect the activity of the catalyst.

22 Claims, 1 Drawing Sheet

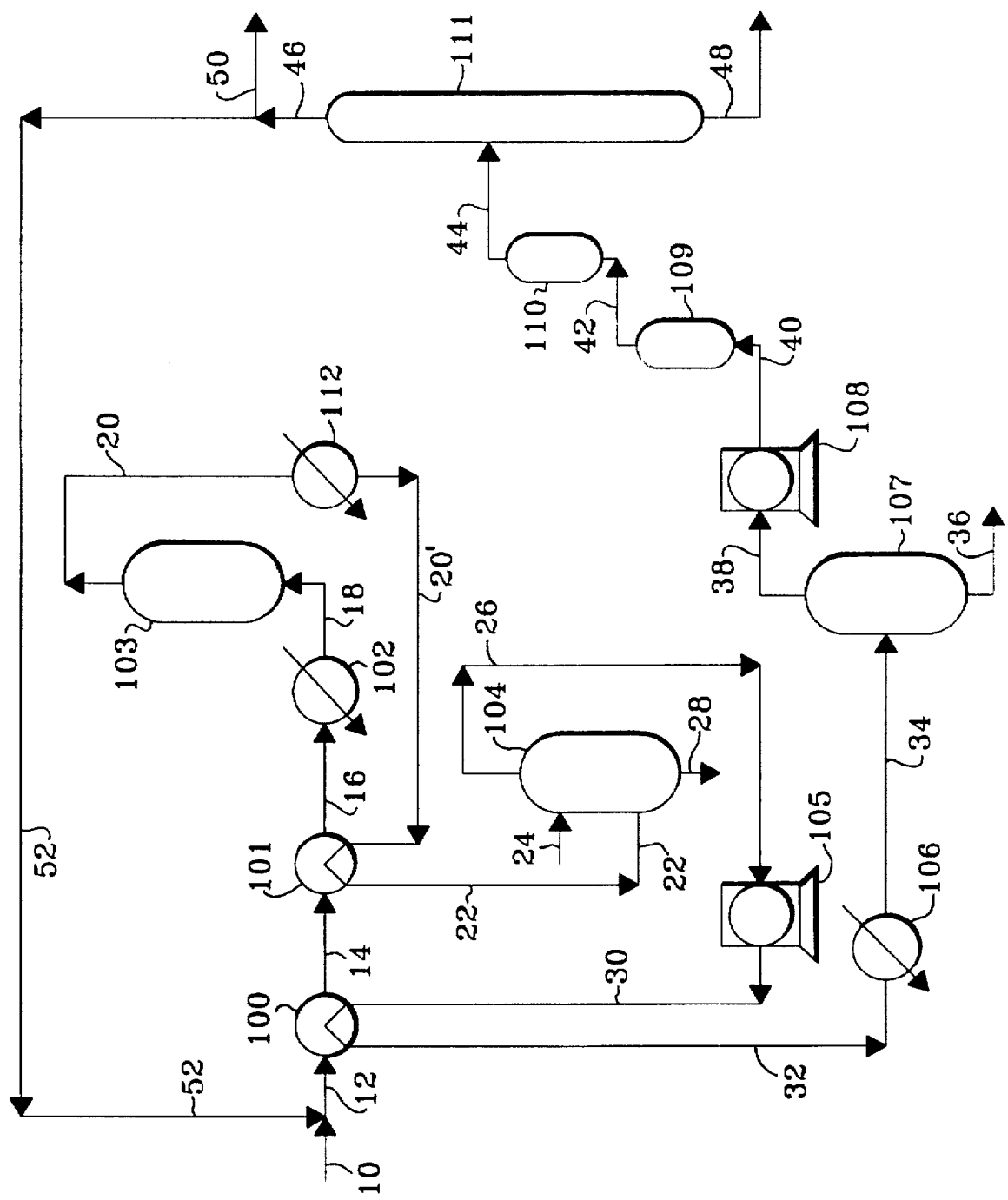

PROCESS FOR PRODUCING LIGHT OLEFINS

FIELD OF THE INVENTION

This invention relates to a process for the production of light olefins from an oxygenate feedstream.

BACKGROUND OF THE INVENTION

Light olefins have traditionally been produced through the process of steam or catalytic cracking. Because of the limited availability and high cost of petroleum sources, the cost of producing light olefins from such petroleum sources has been steadily increasing. Light olefins serve as feeds for the production of numerous chemicals. As the emerging economies of the Third World strain toward growth and expansion, the demand for light olefins will increase dramatically.

The search for alternative materials for light olefin production has led to the use of oxygenates such as alcohols, and more particularly to the use of methanol, ethanol, and higher alcohols or their derivatives. These alcohols may be produced by fermentation or from synthesis gas. Synthesis gas can be produced from natural gas, petroleum liquids, and carbonaceous materials including coal, recycled plastics, municipal wastes, or any organic material. Thus, alcohol and alcohol derivatives may provide non-petroleum based routes for the production of olefin and other related hydrocarbons.

Molecular sieves such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. Nos. 3,928,483, 4,025,575, 4,252,479 (Chang et al.); 4,496,786 (Santilli et al.); 4,547,616 (Avidan et al.); 4,677,243 (Kaiser); 4,843,183 (Inui); 4,499,314 (Seddon et al.); 4,447,669 (Harmon et al.); 5,095,163 Barger); 5,126, 308 (Barger); 4,973,792 (Lewis); and 4,861,938 (Lewis).

The process may be generally conducted in the presence of one or more diluents which may be present in the oxygenate feed in an amount between about 1 and about 99 molar percent, based on the total number of moles of all feed and diluent components fed to the reaction zone (or catalyst). Diluents include—but are not limited to—helium, argon, nitrogen, carbon monoxide, carbon dioxide, hydrogen, water, paraffins, hydrocarbons (such as methane and the like), aromatic compounds, or mixtures thereof. U.S. Pat. Nos. 4,861,938 and 4,677,242 particularly emphasize the use of a diluent combined with the feed to the reaction zone to maintain sufficient catalyst selectivity toward the production of light olefin products, particularly ethylene. One such diluent which has been employed is steam. The above U.S. Patents are hereby incorporated by reference.

U.S. Pat. No. 4,543,435 discloses a process for converting an oxygenated feedstock comprising methanol, dimethyl ether or the like in an oxygenate conversion reactor into liquid hydrocarbons comprising $C_2$–$C_4$ olefins and $C_5^+$ hydrocarbons. The $C_2$–$C_4$ olefins are compressed to recover an ethylene-rich gas is recovered. The ethylene-rich gas is recycled to the oxygenate conversion reactor.

International Patent Application No. 93/13013 to Kvisle et al. relates to an improved method for producing a silicon-alumino-phosphate catalyst which is more stable to deactivation by coking. The patent discloses that after a period of time, all such catalysts used to convert methanol to olefins (MTO) lose the active ability to convert methanol to hydrocarbons primarily because the microporous crystal structure is coked; that is, filled up with low volatility carbonaceous compounds which block the pore structure. The carbonaceous compounds can be removed by conventional methods such as combustion in air.

It has been found that high concentrations of water in the reaction mixture, which are generally required to maintain an appropriate level of dilution, have an adverse effect on the catalyst life and cause the catalyst to deactivate rapidly. Furthermore, water is a by-product of the reaction and its production increases the amount of water seen by the catalyst. Processes are sought which reduce the amount of water in the reaction mixture while maintaining the appropriate level of dilution. These and other disadvantages of the prior art are overcome by the present invention, however, and a new improved process for conversion of oxygenates to hydrocarbons is provided.

SUMMARY OF THE INVENTION

In the present invention, a combination of water production processes is employed to reduce the amount of water at a critical point in the production of light olefins. It was discovered that the use of water or steam as a diluent in an oxygenate conversion process had a deleterious effect on the metal aluminophosphate catalyst. By the process of the present invention, the water in the oxygenate conversion zone is significantly reduced and significant capital and operating cost savings are obtainable. By replacing steam with methane as a diluent and by obtaining the methane from the by-product of the oxygenate conversion reaction, the catalyst life and stability of the metal aluminosilicate catalyst in the oxygenate conversion zone can be improved. Methane, when used as a diluent, will not affect the activity of the catalyst. The availability of methane within the process reduces the treating requirements for preparing an external diluent stream to prevent exposing the catalyst to potentially harmful impurities. Although methane does not provide the thermal and separation advantages of a steam diluent, the use of methane as a diluent significantly reduces the concentration of water in the reaction zone.

The invention provides a process for the production of light olefins having from 2 to 4 carbon atoms per molecule from an oxygenated feedstock. The oxygenated feedstock comprises at least one of the group consisting of an alcohol, an ether, an aldehyde, a ketone, and mixtures thereof. The process comprises passing the feedstock in the presence of a diluent to a reaction zone and therein contacting the feedstock with an ELAPO molecular sieve catalyst selective for the conversion of at least a portion of the feedstock into light olefins to produce a reactor effluent comprising methane and light olefins. The reactor effluent is passed to a separation zone to provide a light hydrocarbon fraction comprising methane and a product fraction comprising light olefins. At least a portion of the light hydrocarbon fraction is recycled to the reaction zone as the diluent.

The preferred ELAPO molecular sieve catalyst for use in the reaction zone is a SAPO catalyst such as SAPO-34 or SAPO-17 and the light olefins produced include ethylene, propylene, and butylene.

In another embodiment, the invention relates to a process for the production of light olefins comprising ethylene and propylene from an oxygenated feedstock comprising at least one of methanol and dimethyl ether. The process comprises passing the oxygenated feedstock in the presence of a diluent comprising methane to a reaction zone. The reaction zone contains a SAPO catalyst selective for the conversion of at least a portion of the oxygenated feedstock into light olefins to produce a reactor effluent comprising water, methane, and light olefins. At least a portion of the water from the reactor effluent is removed to provide a de-watered reactor effluent. The de-watered reactor effluent is passed to a separation zone to provide a light hydrocarbon fraction which is essentially free of ethylene and a light olefin stream. At least a portion of the light hydrocarbon stream is returned to the reaction zone to provide the diluent. The light olefin stream is recovered. The light olefin stream may be further separated into essentially pure ethylene and propylene. Ethylene and propylene are preferably produced at purities of at least 99.9 mol %.

In a further embodiment, the invention is a process for the production of light olefins comprising ethylene and propylene from a feedstock. The feedstock comprises at least one methanol and dimethyl ether. The process comprises admixing the feedstock with a diluent to provide a feed admixture. The feed admixture is passed to a feed/effluent exchanger to heat the feed admixture providing a heated feedstream. The heated feedstream is cooled providing a cooled feedstream and the cooled feedstream is passed to a reaction zone. The reaction zone contains a SAPO catalyst selective for the conversion of at least a portion of the cooled feedstream into light olefins. A reactor effluent stream comprising methane, light olefins, and water is produced in the reaction zone. At least a portion of the methane is separated from the reactor effluent and the portion of the methane is returned to be admixed with the feedstock as the diluent.

BRIEF DESCRIPTION OF THE DRAWINGS

The figure is a schematic process flow diagram illustrating the process of the instant invention employing a methane recycle.

DETAILED DESCRIPTION OF THE INVENTION

In accordance with the process of the present invention, an oxygenate feed is catalytically converted to hydrocarbons containing aliphatic moieties such as—but not limited to—methane, ethane, ethylene, propane, propylene, butylene, and limited amounts of other higher aliphatics by contacting the oxygenate feed with a preselected catalyst. The oxygenate feed comprises hydrocarbons containing aliphatic moieties such as—but not limited to—alcohols, halides, mercaptans, sulfides, amines, ethers and carbonyl compounds or mixtures thereof. The aliphatic moiety preferably contains from about 1 to about 10 carbon atoms, and more preferably 1 to about 4 carbon atoms. Representative oxygenates include—but are not limited to methanol, isopropanol, n-propanol, ethanol, fuel alcohols, dimethyl ether, diethyl ether, methyl mercaptan, methyl sulfide, methyl amine, ethyl mercaptan, ethylchloride, formaldehyde, dimethylketone, acetic acid, n-alkylamines, n-alkylhalides, and n-alkyl-sulfides having alkyl groups of 1 to 10 carbon atoms or mixtures thereof. In a preferred embodiment, methanol is used as the oxygenate feed. In a more preferred embodiment, dimethyl ether is used as the oxygenate feed. The term "oxygenate feed" as employed in the present invention and described herein designates only the organic material used as the feed. The total charge of feed to the reaction zone may contain additional compounds such as diluents.

A diluent is required to maintain the selectivity of the catalyst to produce light olefins, particularly ethylene and propylene. The use of steam as the diluent provides certain equipment cost and thermal efficiency advantages. The phase change between steam and liquid water can be employed to advantage in transferring heat between the feedstock and the reactor effluent, and the separation of the diluent from the product requires simple condensation of the water to separate the water from the hydrocarbons. Ratios of 1 mole of feed to 4 moles of water have been disclosed. It was found that these high levels of water combined with the water produced as a by-product of the reaction resulted in the rapid loss of catalyst activity. Laboratory and pilot plant testing showed that catalyst activity is significantly reduced by combination of a steam diluent and the by-product water levels. The use of methane, a by-product of the conversion reaction, significantly reduces the amount of water in the reaction zone. Preferably the ratio of moles of feed to moles of methane diluent will range from about 1:1 to about 1:5. To illustrate the major differences in thermal efficiency between a steam diluent and a methane diluent scheme, the steam diluent scheme requires a feed heater following a feed/effluent exchanger to raise the combined feedstock to the reaction temperature. When methane is employed, the combined feedstock must be cooled to reach the reaction temperature. The cooling of the combined feedstocks may be accomplished by the direct cooling of the combined feedstock after the feed/effluent exchanger or by the use of a cooler on the reactor effluent stream to reduce the temperature of the reactor effluent prior to the feed/effluent exchanger. The cooling of the reactor feed may be accomplished by generating steam to remove the process heat. It is preferred that at least a portion of the process heat be removed from the combined feedstock prior to entering the reactor. This cooling step also serves as a trim cooler to maintain the temperature of the cooled reactor effluent at a temperature which permits the cooled reactor effluent to be water-scrubbed to remove catalyst fines. If the cooled reactor effluent is too hot, the water-scrubbing step will not be effective and catalyst fines will be introduced to the reactor effluent compressor.

The water concentration in the reaction zone may be reduced further by the use of a feedstock comprising dimethyl ether (DME) rather than methanol. The ratio of methyl groups to oxygen in DME is twice that of methanol resulting in the production of half the production of water for the same amount of light olefin produced.

The process of the present invention is preferably conducted in the vapor phase such that the oxygenate feed is contacted in a vapor phase in a reaction zone with the zeolite catalyst at effective process conditions to produce hydrocarbons, i.e., an effective temperature pressure, WHSV and, optionally, an effective amount of diluent, correlated to produce hydrocarbons. The process is affected for a period of time sufficient to produce the desired light olefin products. In general, the residence time employed to produce the desired product can vary from seconds to a number of hours. It will be readily appreciated that the residence time will be determined to a significant extent by the reaction temperature, the molecular sieve selected, the WHSV, the phase (liquid or vapor) and process design characteristics selected. The feedstock flow rate affects olefin production. Increasing the feedstock flow rate (expressed as weight hourly space velocity, or WHSV) enhances the formation of olefin production relative to paraffin production. However, the enhanced olefin production relative to paraffin production is offset by a diminished conversion of oxygenate to hydrocarbons.

The process is effectively carried out over a wide range of pressures, including autogenous pressures. At pressures between about 0.001 atmospheres (0.76 torr) and about 1000 atmospheres (760,000 torr), the formation of light olefin products will be affected although the optimum amount of product will not necessarily form at all pressures. The preferred pressure is between about 0.01 atmospheres (7.6 torr) and about 100 atmospheres (76,000 torr). The pressures referred to herein for the process are exclusive of the inert diluent, if any, that is present and refer to the partial pressure of the feedstock as it relates to oxygenate compounds and/or mixtures thereof. Pressures outside the stated range are not excluded from the scope of this invention, although such do not fall within certain desirable embodiments of the invention. At the lower and upper end of the pressure range and beyond, the selectivities, conversions and/or rates to light olefin products may not occur at the optimum, although light olefin such as ethylene may still be formed.

The temperature which may be employed in the process may vary over a wide range depending, at least in part, on the selected molecular sieve catalyst. In general, the process can be conducted at an effective temperature between about 200° C. (392° F.) and about 700° C. (1292° F.). Temperatures outside the stated range are not excluded, although they do not fall within certain desirable embodiments of the present invention. At the lower end of the temperature range, and thus, generally at a lower rate of reaction, the formation of the desired light olefin products may become markedly slow. At the upper end of the temperature range and beyond, the process may not form an optimum amount of light olefin products. Notwithstanding these factors, the reaction will still occur and the feedstock, at least in part, can be converted to the desired light olefin products at temperatures outside the range between about 200° C. (392° F.) and about 700° C. (1292° F.).

The selection of a particular catalyst for use in the conversion process depends upon the particular conversion process and other factors known to those skilled in the art which need not be further discussed herein. However, in a preferred aspect of the present invention where an aliphatic hetero compounds are converted into light olefins, it is preferred that the catalysts have relatively small pores. The preferred small pore catalysts are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the catalyst and adsorption of the adsorbate is over three percent by weight of the adsorbate based on the weight of the catalyst. Certain of the catalysts useful in the present invention have pores with an average effective diameter of less than 5 Angstroms. The average effective diameter of the pores of preferred catalysts is determined by measurements described in D. W. Breck, *ZEOLITE MOLECULAR SIEVES* by John Wiley & Sons, New York (1974), hereby incorporated by reference in its entirety. The term effective diameter is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable catalyst may be chosen from among layered clays, zeolitic molecular sieves, and non-zeolitic molecular sieves.

Zeolitic molecular sieves in the calcined form may be represented by the general formula:

$$Me_{2/n}O:Al_2O_3:xSiO_2:yH_2O$$

where Me is a cation, x has a value from about 2 to infinity, n is the cation valence and y has a value of from about 2 to 10.

Typically, well-known zeolites which may be used include chabazite—also referred to as Zeolite D, clinoptilolite, erionite, faujasite—also referred to as Zeolite X and Zeolite Y, ferrierite, mordenite, Zeolite A, Zeolite P, ZSM-5, ZSM-11, and MCM-22. Other zeolites include those having a high silica content, i.e., those having silica to alumina ratios greater than 10 and typically greater than 100 can also be used. One such high silica zeolite is silicalite, as the term used herein includes both the silicapolymorph disclosed in U.S. Pat. No. 4,061,724 and also the F-silicate disclosed in U.S. Pat. No. 4,073,865, hereby incorporated by reference. Detailed descriptions of some of the above identified zeolites may be found in D. W. Breck, supra.

Non-zeolitic molecular sieves include molecular sieves which have the proper effective pore size and are embraced by an empirical chemical composition, on an anhydrous basis, expressed by the empirical formula:

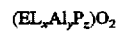

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of metals, x represents the total amount of the metal mixture present. Preferred metals (EL) are silicon, magnesium and cobalt with silicon being especially preferred.

The preparation of various ELAPOs are well known in the art and may be found in U.S. Pat. Nos. 5,191,141 (ELAPO); 4,554,143 (FeAPO); 4,440,871 (SAPO); 4,853,197 (MAPO, MnAPO, ZnAPO, CoAPO); 4,793,984 (CAPO), 4,752,651 and 4,310,440 all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

The reaction mixture is placed in a sealed pressure vessel, optionally lined with an inert plastic material such as polytetrafluoroethylene and heated preferably under autogenous pressure at a temperature between about 50° C. and 250° C. and preferably between about 100° C. and 200° C. for a time sufficient to produce crystals of the ELAPO molecular sieve. Typically the time varies from about 2 hours to about 30 days and preferably from about 4 hours to about 20 days.

The desired product is recovered by any convenient method such as centrifugation or filtration.

It is known that the particle size of the ELAPO molecular sieve can be reduced by stirring the reaction mixture at high speeds (see examples) and by using TEAOH as the templating agent. It is preferred that the ELAPO molecular sieves are composed of particles at least 50% of which have a particle size less than 1.0 μm and no more than 10% of the ELAPO particles have a particle size greater than 2.0 μm.

The ELAPOs which are synthesized using the process described above will usually contain some of the organic templating agent in its pores. In order for the ELAPOs to be active catalyst, the templating agent in the pores must be removed by heating the ELAPO powder in an oxygen containing atmosphere at a temperature of about 200° C. to about 700° C. until the template is removed, usually a few hours.

A preferred embodiment of the invention is one in which the metal (EL) content varies from about 0.005 to about 0.05 mole fraction. If EL is more than one metal, then the total concentration of all the metals is between about 0.005 and 0.05 mole fraction. An especially preferred embodiment is one in which EL is silicon (usually referred to as SAPO). The SAPOs which can be used in the instant invention are any of those described in U.S. Pat. Nos. 4,440,871; 5,126,308, and 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å. Another SAPO, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 Å and less than about 5.0 Å.

The preferred catalyst may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength, and the like to the solid particles. Such matrix materials are often, to some extent, porous in nature and may or may not be effective to promote the desired hydrocarbon conversion. The matrix materials may promote conversion of the feedstream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like.

If matrix materials, e.g., binder and/or filler materials, are included in the catalyst composition, the non-zeolitic and/or zeolitic molecular sieves preferably comprise about 1% to 99%, more preferably about 5% to about 90% and still more preferably about 10% to about 80%, by weight of the total composition. The preparation of solid particles comprising catalyst and matrix materials is conventional and well known in the art and, therefore, need not be discussed in detail herein.

DETAILED DESCRIPTION OF THE DRAWINGS

The process of the present invention is hereinafter described with reference to the drawing which illustrates various aspects of the process. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation systems, etc. It may also be discerned that the process flow depicted in the drawing may be modified in many aspects without departing from the basic overall concept of the invention.

With reference to the drawing, an oxygenated feedstock comprising at least one of the group consisting of an alcohol, an ether, an aldehyde, a ketone, and mixtures thereof in line 10 is admixed with a diluent 52 and the admixture is passed via line 12 to a first heat exchanger 100 to preheat the feedstock/diluent admixture by cross exchange and to provide a preheated feedstream 14. The preheated feedstream 14 is passed to a second heat exchanger 101 wherein the preheated feedstream is exchanged with a reactor effluent stream 20 to provide a heated feedstream 16 and a cooled reactor effluent stream 22. The heated feedstream 16 is passed to a reactor cooler 102 to cool the reactor feedstream 18 to reaction conditions including a reaction temperature ranging from about 350° C. to about 525° C. and a pressure of about 1 to about 5 atmospheres. The reactor feedstream is passed to a reaction zone 103 containing a SAPO catalyst selective for the conversion of at least a portion of the reactor feedstream 18 into $C_2$–$C_4$ olefins and to produce a reactor effluent stream 20. The reactor effluent stream 20 and 20' comprising methane, water, and light olefins is passed to the second heat exchanger 101 to provide the cooled reactor effluent stream 22. In an alternate embodiment, the reactor effluent stream 20 is passed to a steam generator 112 to cool the reactor effluent by removing a portion of the process heat and providing a first cooled reactor effluent in line 20'. The first cooled reactor effluent 20' is passed to the second heat exchanger 101, further cooling the reactor effluent and providing the cooled reactor effluent stream 22. The cooled reactor effluent stream 22 is passed to a water scrubber zone 104 wherein the cooled reactor effluent stream 22 is contacted with a water wash stream 24 to remove catalyst fines from the cooled reactor effluent stream 22 in an aqueous stream 28. It is necessary to remove catalyst fines from the cooled effluent stream prior to further compressing the cooled reactor effluent stream in preparation for the separation of the individual components. The aqueous stream 28 is withdrawn for further treatment (not shown). A water scrubbed stream 26 is withdrawn from the water scrubber zone 104 and passed to reactor effluent compressor 105 to raise the pressure of the water scrubbed stream 26 and to provide a compressed effluent stream 30. The compressed effluent stream 30 is cross exchanged with the feedstock/diluent admixture 12 in the first heat exchanger 100 to preheat the admixture 12 and to first cool the compressed effluent stream 30 to provide a first cooled compressed effluent stream 32. This permits the recovery of low grade heat in exchanger 100. The first cooled compressed effluent stream 32 is further cooled in condenser 106 to condense at least a portion of the water in the effluent stream 32 and to provide a condensed effluent stream 34. The condensed effluent stream 34 is passed to a flash zone 107 to separate the condensed effluent stream 34 into a hydrocarbon stream 38 and a second aqueous stream 36. The second aqueous stream 36 is passed to an off-site water treatment zone (not shown). The hydrocarbon stream 38 comprising the light olefins and methane is passed to compressor 108 to provide a compressed hydrocarbon stream 40. Preferably, the compressed hydrocarbon stream 40 will be at a pressure of from about 2000 kPa to about 4000 kPa, and more preferably stream 40 will be at a pressure ranging from about 3000 kPa to about 4000 kPa. The compressed hydrocarbon stream 40 is passed to a water removal zone 109 containing a desiccant to reduce the amount of water in the hydrocarbon stream to less than about 1 ppm-vol and to provide a dry hydrocarbon stream 42. The dry hydrocarbon stream 42 is passed to an acid gas removal zone 110, containing an adsorbent selective for the removal of acid gases such as $CO_2$ from the dry hydrocarbon stream 42 and to provide an acid gas reduced stream 44. The acid gas reduced stream 44 is passed to a demethanizer 111 wherein the methane is recovered in an overhead stream 46 and the light olefins comprising $C_2$–$C_4$ are recovered in a bottoms stream 48. It is preferred that the overhead stream 46, which comprises a light hydrocarbon fraction, comprises from about 75 to about 99.9 mol % methane; thus, it is essentially all methane and is essentially free of ethylene. The ethylene content of the overhead stream is preferably less than 5 mol % and more preferably the ethylene content of the overhead stream is less than 1 mol %. The bottom stream 48 is passed to further fractionation (not shown) for recovery of essentially pure ethylene and propylene at purities greater than about 99 mol % and more preferably at purities greater than 99.9 mol %. At least a portion of the overhead stream 52 is returned to be admixed with the feedstock 10 as the diluent and a portion of the overhead stream 42 are withdrawn in line 50 as a fuel stream. Preferably the molar ratio of the diluent in the feed admixture will range from about 1.8 to about 2.3.

EXAMPLES

Example I

A series of runs to determine the effect of accelerated hydrothermal aging on the catalyst of the present invention was carried out. The aged catalyst was evaluated to determine the effect of the aging on the catalyst activity. A 40 gram sample of SAPO-34 catalyst was placed in a 2.2 cm (⅞ inch) I.D. tubular monel reactor forming a catalyst bed therein. The reactor was fitted with stainless steel sintered frits at the bottom of the catalyst bed and on the reactor outlet above the catalyst bed. An air purge flowing up from the bottom to the top of the catalyst bed was established to fluidize the catalyst bed. The pressure was increased to about 793 kPa (100 psig) and the temperature was raised from room temperature to about 460° C. When the temperature stabilized, the air flow was replaced with water at a rate of about 90 grams/hour. The steaming of the catalyst in this manner continued for a series of specified times ranging from about 5 hours to about 200 hours. At the end of the specified time, the water flow was replaced with air and the reactor was cooled to about 100° C. and depressurized.

A portion of the fresh and hydrothermally aged catalyst of approximately 10 grams each was loaded into a 2.2 cm (⅞ inch) I.D., porcelain-lined stainless steel reactor. The catalyst sample was pre-treated with flowing nitrogen at about 435° C. for about 1 hour to dry the catalyst and raise the temperature of the catalyst bed. The nitrogen was replaced with a mixture of methanol and water containing about 80 wt % methanol at a feed rate of about 12.5 grams per hour and at a pressure of about 138 kPa (5 psig). The time, or on-stream time, from the start of the reaction to the point at which the conversion of methanol (and DME) dropped to 99% was recorded. The performance of the catalyst was monitored using an on-line GC measuring the composition of the reactor effluent. The results of this accelerated hydrothermal aging are shown in Table 1. The hydrothermal aging of the SAPO-34 catalyst showed a progressive loss in catalyst ranging from about 4.8 hours for fresh catalyst to about 3.5 hours for a catalyst sample after 100 hours of steaming.

TABLE 1

| HYDROTHERMAL AGING TESTS OF SAPO-34 HOURS ON STREAM AT >99% CONVERSION | |
|---|---|
| FRESH CATALYST | 4.8 |
| 5 HOURS STEAMING | 4.5 |
| 25 HOURS STEAMING | 4.3 |
| 100 HOURS STEAMING | 3.5 |

Example II

The evaluation of the effect of the accelerated hydrothermal aging on conversion for the fresh catalyst and the 100 steaming hour samples of Example I was continued. The conversion was recorded as a function of time from the introduction of the feed. The effect of the continued hydrothermal aging of the catalyst is shown in Table 2. For the fresh catalyst and the 100 hour aged catalyst, the conversion dropped to about 20% after on-stream times ranging from about 5 to about 6.3 hours, with the steamed catalyst exhibiting a more pronounced reduction in conversion at an earlier on-stream time than the feed catalyst. Although the accelerated hydrothermal testing showed that steaming the catalyst results in the permanent loss of catalyst activity, this steaming was evaluated at levels well beyond water levels which would normally be encountered when water or steam is employed as a diluent.

TABLE 2

| EFFECT OF STEAMING ON MTO CATALYST | | |
|---|---|---|
| CONVERSION, % | FRESH CATALYST | 100 HOURS AGING |
| 99 | 4.8 | 3.5 |
| 50 | 5.7 | 4.5 |
| 20 | 6.3 | 5.2 |

Example III

A comparison of a heat balance for a methanol/water diluent scheme with a heat balance for a DME/methane diluent scheme, according to the process flow scheme shown in the Figure, indicates significant differences in the amount of heat exchanger duty required. The methanol/water scheme (A) comprises passing a methanol feedstream admixed with liquid water to the first heat exchanger 100 to preheat the feedstock/diluent admixture and provide a preheated feedstream 14. The preheated feedstream is passed to the second heat exchanger to vaporize the preheated feedstream by cross-exchange with the reactor effluent stream. No reactor cooler is required to cool the heated feedstream prior to introducing the heated feedstream to the reactor. The DME/methane scheme (1) represents an operation wherein the amount of water contacting the catalyst has been reduced significantly. Methane replaces steam as the diluent, and DME rather than methanol is employed as the main reactant. DME produces about half the water in the formation of light olefins than produced by the conversion of methane. In scheme B, the DME/methane admixture, as a vapor, is preheated to a first temperature in the first exchanger. The preheated DME/methane admixture is passed to a second heat exchanger to provide a heated reactor feedstream by cross exchange with the reactor effluent such that the reactor effluent is reduced to a temperature at which the cooled reactor effluent can be a water scrubbed in the conventional manner. The reactor feedstream is cooled in cooler 102 to the reactor temperature. Table 3 illustrates the relative heat exchanger duties for the DME/methane scheme relative to the methanol/water scheme. The primary difference between the methanol/water diluent scheme (A) and the DME methane (B) is the relative thermal efficiency of the scheme which can be characterized as follows:

$$\left[1 - \frac{\text{UTILITY DUTY}}{\text{PROCESS DUTY}}\right]$$

wherein the utility duty is the sum of the condenser and feed heater duties, and the process duty is the sum of the combined effluent feed exchanger duty and any steam generation duty. Thus, the process thermal efficiency is 1 minus the ratio of the external heat requirement to the heat generated by the process. The thermal efficiency of scheme A was 81% and the thermal efficiency of scheme B was 22%. The steam generation shown in the feed heater for case B represents cooling of the feed prior to passing the feed to the reactor. In fact, the cooling of the feed may be accomplished by directly cooling the feed or by removing a portion of the heat from the reactor effluent, thereby reducing the amount of heat transferred to the reactor feed. As shown in the Table 3, the first heat exchanger 100 requires a duty of only 7 percent of a similar heat exchanger in a methanol/water scheme. Similarly, the second heat exchanger 101 duty is reduced to about 81 percent and the feed heater of the methanol/water scheme is a feed cooler in the DME/methane scheme. In addition, the DME methane scheme has a 64% lower heat removal duty in the reaction zone than the methanol/water scheme. Because there is no phase change in the methane diluent scheme, the condenser 106 duty is increased relative to the water diluent scheme.

TABLE 3

| RELATIVE HEATER DUTY REQUIREMENTS | | |
|---|---|---|
| | METHANOL/ WATER SCHEME | DME/METHANE SCHEME |
| EXCHANGER 100 | 1 | 0.07 |
| EXCHANGER 101 | 1 | 0.81 |
| FEED HEATER** 102 | 1 | -7.2 |
| CONDENSER 106 | 1 | 1.8 |
| REACTOR* 103 | 1 | 0.36 |

*REACTOR REQUIRES HEAT REMOVAL
**DME/METHANE SCHEME REQUIRES A FEED COOLER (BY STEAM GENERATION) TO REMOVE PROCESS HEAT PRIOR TO THE REACTION ZONE

We claim:

1. A process for the production of light olefins comprising olefins having from 2 to 4 carbon atoms per molecule from an oxygenated feedstock, having from about 1 to about 4 carbon atoms per molecule, said oxygenated feedstock comprising at least one of the group consisting of an alcohol, an ether, an aldehyde, a ketone, and mixtures thereof, said process comprising:
   a) passing the feedstock to a reaction zone at reaction conditions effective to produce said light olefins and therein contacting said feedstock in the presence of a diluent with an ELAPO molecular sieve catalyst selective for the conversion of at least a portion of said feedstock into said light olefins and water to produce a reactor effluent comprising methane and said light olefins;
   b) passing said reactor effluent to a separation zone to provide a light hydrocarbon fraction comprising methane and a product fraction comprising light olefins; and, c) recycling at least a portion of said light hydrocarbon fraction to said reaction zone as said diluent.

2. The process of claim 1 further comprising removing at least a portion of said water from said reactor effluent prior to passing said reactor effluent to said separation zone.

3. The process of claim 1 wherein said ELAPO molecular sieve catalyst is characterized by an empirical composition an anhydrous basis by the formula:

$$(EL_xAl_yP_z)O_2$$

where EL is an element selected from the group consisting of silicon, magnesium, zinc, iron, cobalt, nickel, manganese, chromium, and mixtures thereof, x is the mole fraction of EL and is at least 0.005, y is the mole fraction of Al and is at least 0.01, and z is the mole fraction of P and is at least 0.01 and x+y+z=1.

4. The process of claim 1 wherein said ELAPO molecular sieve catalyst is selected from the group consisting of SAPO-34, SAPO-17, and mixtures thereof.

5. The process of claims 1 wherein said reactor effluent comprises ethylene and propylene and said light hydrocarbon fraction consists of essentially of methane.

6. The process of claim 5 wherein said light hydrocarbon fraction comprises from about 75 to about 99.9 mol % methane.

7. The process of claim 1 wherein said separation zone comprises a demethanizer tower to provide said light hydrocarbon fraction essentially free of ethylene.

8. A process for the production of light olefins comprising ethylene and propylene from an oxygenated feedstock comprising at least one of methanol and dimethyl ether, said process comprising:
   a) passing said feedstock in the presence of a diluent comprising methane to a reaction zone with a SAPO catalyst at reaction conditions selective for the conversion of at least a portion of said feedstock into said light olefins to produce a reactor effluent comprising water, methane, and said light olefins;
   b) removing at least a portion of said water from said reactor effluent to provide a de-watered reactor effluent;
   c) passing said de-watered reactor effluent to a separation zone to provide a light hydrocarbon fraction essentially free of ethylene and a light olefin stream;
   d) returning at least a portion of said light hydrocarbon stream to said reaction zone to provide said diluent; and
   e) recovering said light olefin stream.

9. The process of claim 8 further comprising separating said light olefin stream to provide an ethylene product stream and a propylene product stream.

10. The process of claim 8 wherein said SAPO catalyst comprise SAPO-34.

11. The process of claim 8 wherein said SAPO catalyst comprises SAPO-17.

12. A process for the production of light olefins comprising ethylene and propylene from a feedstock comprising at least one of methanol and dimethyl ether, said process comprising:
   a) admixing said feedstock with a diluent to provide a feed admixture and passing said admixture to a feed/effluent exchanger to heat the feed admixture to provide a heated feedstream;
   b) cooling said heated feedstream to provide a cooled feedstream and passing the cooled feedstream at reaction conditions to a reaction zone containing a SAPO catalyst selective for the conversion of at least a portion of said cooled feedstream into said light olefins to produce a reactor effluent stream comprising methane, light olefins and water; and c) separating at least a portion of said methane from said reactor effluent and returning said portion to be admixed with said feedstock as said diluent.

13. The process of claim 12 further comprising recovering said light olefins.

14. The process of claim 13 wherein said light olefins comprise ethylene and propylene.

15. The process of claim 14 further comprising separating an ethylene product stream comprising at least about 99.9 mol % ethylene from said reactor effluent.

16. The process of claim 14 further comprising separating a propylene product stream comprising at least about 99.9 mol% propylene from said reactor effluent.

17. The process of claim 12 wherein said SAPO catalyst comprises SAPO-34.

18. The process of claim 1 wherein said diluent is present in said feed admixture in a ratio ranging from about 1.8 to about 2.3.

19. A process for the production of light olefins comprising ethylene and propylene from a feedstock comprising dimethyl ether, said process comprising:

a) admixing said feedstock with a diluent comprising methane to provide a feed admixture and passing said feed admixture to a first heat exchanger to heat said feed admixture to provide a first heated feedstream and passing said first heated feedstream to a second heat exchanger to provide a reactor feedstream;

b) passing said reactor feedsteam at reaction conditions to a reaction zone containing a catalyst selected from the group of SAPO-17, SAPO-34, and mixtures thereof selective for the conversion of at least a portion of said reactor feedstream to produce a reactor effluent stream comprising methane, light olefins, and water;

c) passing said reactor effluent to a steam generator to provide a first cooled effluent stream and passing the first cooled effluent stream to said second heat exchanger to further cool said first cooled effluent by cross exchange with said first heated feedstream to provide a second cooled effluent stream;

d) water scrubbing the second cooled effluent stream in a water scrubber zone to provide a water scrubbed stream, compressing said water scrubbed stream to provide a compressed effluent stream, and cross-exchanging said compressed effluent stream with said feed admixture in said first heat exchanger to provide a cooled compressed effluent stream;

and e) flashing and drying said cooled compressed effluent stream to provide a dry hydrocarbon stream and fractionating said dry hydrocarbon stream to recover a methane stream and said light olefins and recycling at least a portion of said methane to provide said diluent.

20. The process of claim 19 wherein said water scrubbed stream is compressed to a pressure ranging from about 3000 kPa to about 4000 kPa.

21. The process of claim 19 wherein said methane stream comprises less than about 5 mol % ethylene.

22. The process of claim 19 further comprising passing said dry hydrocarbon stream to an adsorption zone containing an adsorbent selective for the removal of said gases prior to said fractionating.

* * * * *